(12) United States Patent
Teicher et al.

(10) Patent No.: US 11,013,455 B2
(45) Date of Patent: May 25, 2021

(54) APPARATUS AND METHOD FOR INSPECTING SKIN LESIONS

(71) Applicant: TYTO CARE LTD., Netanya (IL)

(72) Inventors: Mordechai Teicher, Hod Hasharon (IL); David Gilad-Gilor, Even Yehuda (IL); Eyal Bychkov, Hod Hasharon (IL)

(73) Assignee: TYTO CARE LTD., Netanya (IL)

( * ) Notice: Subject to any disclaimer, the term of this patent is extended or adjusted under 35 U.S.C. 154(b) by 286 days.

(21) Appl. No.: 15/580,757

(22) PCT Filed: Jun. 7, 2016

(86) PCT No.: PCT/IL2016/050591
§ 371 (c)(1),
(2) Date: Dec. 8, 2017

(87) PCT Pub. No.: WO2016/199134
PCT Pub. Date: Dec. 15, 2016

(65) Prior Publication Data
US 2018/0146911 A1 May 31, 2018

Related U.S. Application Data

(60) Provisional application No. 62/173,476, filed on Jun. 10, 2015.

(51) Int. Cl.
G01B 11/26 (2006.01)
A61B 5/00 (2006.01)
(Continued)

(52) U.S. Cl.
CPC ............ *A61B 5/444* (2013.01); *A61B 5/0077* (2013.01); *A61B 5/6844* (2013.01); *A61B 5/748* (2013.01);
(Continued)

(58) Field of Classification Search
CPC ....... A61B 5/444; A61B 5/748; A61B 5/7475; A61B 5/6844; A61B 5/0077;
(Continued)

(56) References Cited

U.S. PATENT DOCUMENTS 5,836,872 A 11/1998 Kenet et al.
8,213,695 B2 * 7/2012 Zouridakis ........... A61B 5/0059
382/128
(Continued)

OTHER PUBLICATIONS

"IMI National Guidelines: Guide to Good Practice: Mole Mapping", UK Institute of Medical Illustrators, Feb. 2, 2013. Entire Document.
(Continued)

*Primary Examiner* — Amelie R Davis
*Assistant Examiner* — Adil Partap S Virk

(57) ABSTRACT

A user moves a handheld inspection device toward a skin region that includes a target skin lesion. A current image of the skin region or part thereof that includes the target skin lesion as currently taken by the handheld inspection device is displayed on a screen, with the target skin lesion marked. When reaching a close distance from the target skin lesion, a close-up inspection is performed. If the target skin lesion is missing in the current image, the close-up inspection process is interrupted, and the user is instructed to move the handheld inspection device to a remote distance from the skin region for restarting the inspection process.

18 Claims, 13 Drawing Sheets

(51) Int. Cl.
 *G06T 7/00* (2017.01)
 *G01S 17/08* (2006.01)
(52) U.S. Cl.
 CPC .......... *A61B 5/7475* (2013.01); *G06T 7/0012* (2013.01); *A61B 2560/0431* (2013.01); *G01B 11/26* (2013.01); *G01S 17/08* (2013.01); *G06T 2207/30088* (2013.01); *G06T 2207/30096* (2013.01)
(58) Field of Classification Search
 CPC ............ A61B 2560/0431; G01B 11/26; G06T 7/0012; G06T 2207/30088; G06T 2207/30096; G01S 17/08
 See application file for complete search history.

(56) References Cited

U.S. PATENT DOCUMENTS

| | | |
|---|---|---|
| 8,337,405 B2 | 12/2012 | Waagen et al. |
| 8,543,519 B2 | 9/2013 | Guyon et al. |
| 8,837,832 B2 | 9/2014 | Kislal |
| 8,908,927 B2 | 12/2014 | Atsmon et al. |
| 2009/0028442 A1 | 1/2009 | Kimmel et al. |
| 2009/0213213 A1* | 8/2009 | Fright .................. A61B 5/1077 348/77 |
| 2009/0279760 A1* | 11/2009 | Bergman .................. G06T 7/44 382/128 |
| 2009/0326383 A1 | 12/2009 | Barnes et al. |
| 2010/0302358 A1* | 12/2010 | Chen ...................... A61B 5/445 348/77 |
| 2011/0054310 A1* | 3/2011 | Taylor .................... A61B 5/445 600/425 |
| 2012/0008838 A1* | 1/2012 | Guyon ...................... G06T 7/66 382/128 |
| 2012/0035469 A1* | 2/2012 | Whelan ................ A61B 5/0077 600/425 |
| 2013/0307950 A1 | 11/2013 | Aharon |
| 2013/0322711 A1* | 12/2013 | Schultz .................. A61B 5/445 382/128 |
| 2014/0036054 A1* | 2/2014 | Zouridakis ........... A61B 5/0077 348/77 |
| 2014/0088440 A1 | 3/2014 | Swart et al. |
| 2014/0126787 A1* | 5/2014 | Zuhlke Kimball ... G06T 7/0012 382/128 |

OTHER PUBLICATIONS

Hartley et al, "Multiple view geometry in computer vision", Cambridge university press, second edition 2003, pp. 1-673.

Bhatia et al, "3d human limb detection using space carving and multi-view eigen models", Computer Vision and Pattern Recognition Workshop, 2004. CVPRW'04. Conference on. IEEE, 2004, pp. 1-7.

Bhuiyan et al, "Image processing for skin cancer features extraction", International Journal of Scientific & Engineering Research, vol. 4, Issue 2, Feb. 2013; pp. 1-6.

Blum et al, "Digital image analysis for diagnosis of skin tumors", Seminars in Cutaneous Medicine and Surgery. vol. 27, No. 1, Frontline Medical Communications, 2008, pp. 11-15.

* cited by examiner

The set of 19 standard views begins with:

- D1 Upper body AP (from under chin to pelvis, not including arms)
- D2 Upper body PA (from neck hairline to pelvis, not including arms)
- D3 Upper body Right Lateral (from under chin to pelvis - arm raised)
- D4 Upper body Left Lateral (from under chin to pelvis - arm raised)
- D5 Lower body AP (from pelvis to soles of feet)
- D6 Lower body PA (from pelvis to soles of feet)
- D7 Lower body Right Lateral (from pelvis to soles of feet)
- D8 Lower body Left Lateral (from pelvis to soles of feet)
- D9 Right arm AP (arm held horizontally, from shoulder to finger tip)
- D10 Left arm AP (arm held horizontally, from shoulder to finger tip)
- D11 Right arm PA (arm held horizontally, from shoulder to finger tip)
- D12 Left arm PA (arm held horizontally, from shoulder to finger tip)

The following views are considered supplementary:

- D13 Both hands Dorsal
- D14 Both hands Palmer
- D15 Both feet Dorsal
- D16 Both feet Plantar
- D17 Head and Neck AP
- D18 Head and Neck Right Lateral
- D19 Head and Neck Left Lateral

FIG. 2B

APPARATUS AND METHOD FOR INSPECTING SKIN LESIONS

CROSS REFERENCE TO RELATED APPLICATIONS

This application claims the benefits of U.S. provisional patent application No. 62/173,476 filed on Jun. 10, 2015, which is incorporated by reference in its entirety as if set forth herein.

BACKGROUND OF THE INVENTION

Field of the Invention

The present invention relates to medical examination, and in particular to the inspection of skin lesions for early detection of skin cancer.

Description of Related Art

Skin lesions are sometimes inspected for early detection of developing skin cancer, where early intervention is the best way to avoid or recover from an otherwise fatal disease. Using bare-eye inspection, suspect lesions can be roughly detected by their shape, borders, color, size, and by changes in the above over time. Enlarged, high-resolution color images are helpful, while sophisticated inspection technologies and techniques, generally termed "dermatoscopy", provide more reliable results at an earlier stage. Digital dermatoscopy combines knowledge from computer imaging, image processing and medicine, for computer-assisted or automated early detection of suspect skin lesions. U.S. Pat. Nos. 5,836,872, 8,213,695, 8,337,405, 8,543,519, 8,837,832 and 8,908,927 are examples of technologies related to digital dermatoscopy.

A typical person may have tens to hundreds of skin lesions, most of which are and will remain harmless. A visit to a dermatologist, including full-body visual screening, sometimes with assistance of dermatoscopy, may identify and document those few selected skin lesions that either necessitate immediate intervention, or require attention and periodic inspection for detecting changes.

Periodic inspection of selected skin lesions can be carried out at home, by the patient and/or with the aid of a family member or another person. Calendar reminders can encourage timely skin inspections, while a database that includes images and features of the selected skin lesions can help in both ensuring that all selected skin lesions are inspected, and in detecting changes—such changes being the most dependable patient-level inspection method for triggering a visit to a dermatologist for further assessment.

Periodic inspection of selected skin lesions at home may be tedious and error-prone for many, especially those who have numerous skin lesions to inspect, with some surrounded by other skin lesions, which may lead to confusion.

BRIEF SUMMARY OF THE INVENTION

Object of the Present Disclosure

The present disclosure teaches methods and systems for assisting users in carrying out inspection of skin lesions.

Definitions

By "skin lesion" is meant herein a visually-detectable spot on the skin, such as a skin mole (nevus), freckle, sun spot, rash or wound. By "selected skin lesions" herein is meant skin lesions selected for inspection. By "target skin lesion" is meant herein a skin lesion that is to be currently examined.

By "patient" is meant herein a person having skin lesions to be inspected using the teachings of the present disclosure. By "user" is meant herein a person performing a method or using a system taught by the present disclosure. A user may be the patient, or another person assisting a patient.

SUMMARY

According to preferred embodiments of the present invention, there is provided a process of close-up inspection of at least one skin lesion within a region on a skin surface, the region containing multiple skin lesions, the process including: (a) in a handheld inspection device, positioned by a user at a remote distance from the skin surface, the remote distance being effectives for acquiring an image of the region by the handheld inspection device: acquiring an image of the region; (b) in a processor: selecting a target skin lesion within the image of the region; (c) on a screen: (i) displaying the image of the region, and (ii) marking the target skin lesion within the image of the region, to visually distinguish the target skin lesion from other skin lesions within the region; (d) while the handheld inspection device is moved by the user toward the skin surface: (i) in the handheld inspection device: continuously acquiring a current image of the skin surface, and (ii) in the processor and on the screen: showing and marking the target skin lesion within the current image of the skin surface, and, if the target skin lesion is not included within the current image of the skin surface, interrupting the process of close-up inspection and instructing the user to restart the process of close-up inspection from a remote distance; and (e) in the handheld inspection device: in a close distance that is less than the remote distance and is sufficiently close to the skin surface for performing a close-up inspection of the target skin lesion: performing the close-up inspection of the target skin lesion.

The process may further include illuminating the target skin lesion. The close-up inspection may include at least one of: acquiring a high-resolution image of the target skin lesion, extracting features of the target skin lesion, or performing digital dermatoscopy of the target skin lesion. Furthermore, the close-up inspection may further include projecting from the handheld inspection device at least one laser beam illuminating within or in proximity to the target skin lesion, and performing at least one of: visually identifying the target skin lesion on the skin surface, measuring a distance between the handheld inspection device and the skin surface, or measuring an angle between the handheld inspection device's optical axis and the skin surface.

There is also provided a system for close-up inspection of at least one skin lesion within a region on a skin surface, the region containing multiple skin lesions, the system including: (a) a handheld inspection device that can be positioned at selectable distances from the skin surface, the handheld inspection operable to, at least: (i) acquire skin images, (ii) from a remote distance: acquire an image of the region, and (iii) from a close distance that is closer to the skin surface than the remote distance: perform a close-up inspection of a skin lesion; (b) a screen operable to, at least: (i) display skin images captured by the handheld inspection device, and (ii) display a processor-generated marker to visually distinguish a selected skin lesion within a skin image that contains multiple lesions; and a processor programmed to, at least: (i) receive an image from the handheld inspection device, (ii)

check whether the image received from the handheld inspection device includes a target skin lesion, (iii) if the check is negative: interrupt the close-up inspection and instruct the user to restart the process of close-up inspection from a remote distance, (iv) if the check is positive: generate a current image that includes the image received from the handheld inspection device with the target skin lesion image marked by a marker, and (v) send the current image to the screen.

The close-up inspection performed by the system may include illuminating the target skin lesion. The screen and the processor may form part of the handheld inspection device, or the system may further include a computer that is separate from the handheld inspection device, with the screen and the processor forming part of the computer.

The close-up inspection performed by the system may further include at least one of: acquiring a high-resolution image of the target skin lesion, or performing digital dermatoscopy of the target skin lesion. The close-up inspection may further include extracting features of the target skin lesion.

The handheld inspection device included in the system may further include a laser projecting at least one laser beam for illuminating within or in proximity to the target skin lesion for at least one of: (i) visually identifying the target skin lesion on the skin surface, (ii) measuring a distance between the handheld inspection device and the skin surface, or (iii) measuring an angle between the handheld inspection device's optical axis and the skin surface.

There is also provided a handheld inspection device for close-up inspection of at least one skin lesion within a region of a skin surface, the region containing multiple skin lesions, the handheld inspection device including: (a) a camera operable to, at least: (i) acquire skin images, (ii) from a remote distance: acquire an image of the region, and (iii) from a close distance that is closer to the skin surface than the remote distance: perform a close-up inspection of a skin lesion; (b) a screen operable to, at least: (i) display skin images captured by the camera, and (ii) display a processor-generated marker to visually distinguish a selected skin lesion within a skin image that contains multiple lesions; and (c) a processor programmed to, at least: (i) receive an image from the camera, (ii) check whether the image received from the camera includes a target skin lesion, (iii) if the check is negative: interrupt the close-up inspection and instruct the user to restart the process of close-up inspection from a remote distance, (iv) if the check is positive: generate a current image that includes the image received from the camera with the target skin lesion image marked by a marker, and send the current image to the screen.

The handheld inspection device may further include other sensors, and the close-up inspection may further include performing, with participation of the other sensors, digital dermatoscopy of the target skin lesion. The handheld inspection device may include an illuminator, and the close-up inspection may include illuminating the target skin lesion. Also, the handheld inspection device may further include a laser projecting at least one laser beam for illuminating within or in proximity to the target skin lesion for at least one of: (i) visually identifying the target skin lesion on the skin surface, (ii) measuring a distance between the handheld inspection device and the skin surface, or measuring an angle between the handheld inspection device's optical axis and the skin surface. The close-up inspection may include acquiring a high-resolution image of the target skin lesion, and may further perform extracting features of the target skin lesion.

BRIEF DESCRIPTION OF SEVERAL VIEWS OF THE DRAWINGS

FIGS. 2A-2B are illustrations describing an exemplary division of a skin surface into regions.

DETAILED DESCRIPTION OF PREFERRED EMBODIMENTS OF THE INVENTION

The present disclosure describes a system and method for inspecting skin lesions by using at least a handheld inspection device. FIGS. 1A-D depict several embodiments, with varying cooperation of the handheld inspection device with a computer and/or a server.

A Standalone Handheld Inspection Device

Figure 1A:
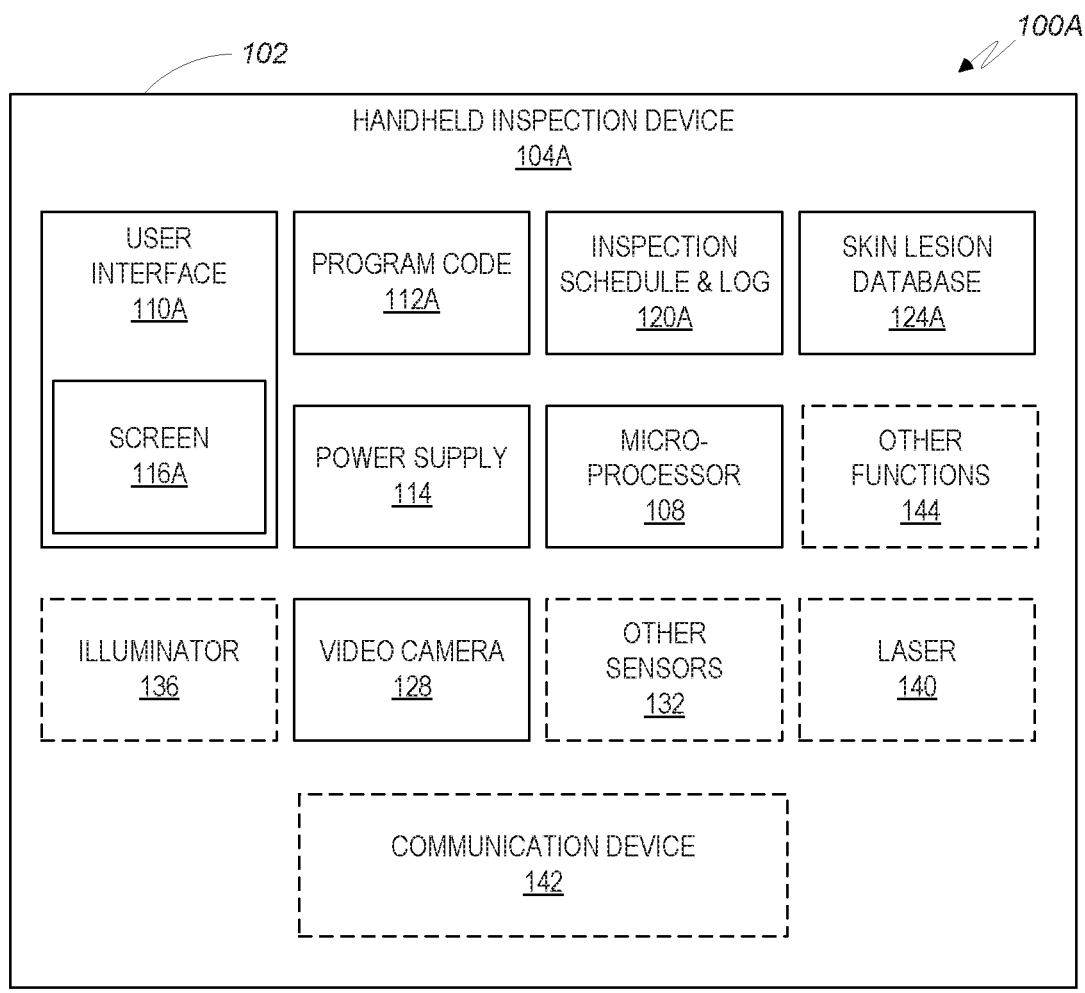
FIGS. 1A-1D are block diagrams depicts four configurations of systems according to preferred embodiments of the present invention.

Reference is made to FIG. 1A that describes system 100A composed of handheld inspection device 104A. Enclosure 102 hosts elements represented by the blocks of FIG. 1A, either as permanent components or as temporary attachments, or as combination thereof; for example, video camera 128 may include permanent sensor and optics that form part of handheld inspection device 104A, enhanced by temporarily-attached additional optics. Microprocessor 108 executes program code 112A to perform the functions of system 100A described below. User interface 110A includes customary I/O elements, such as keys, buttons, microphone, speaker, vibration generator, and specifically screen 116A, which may be a touchscreen, that provides guidance to the user during the operation of handheld inspection device 104A. Inspection schedule & log 120A includes a list of past and future inspection events, and is optionally used to trigger reminders via user interface 110A. Video camera 128 includes one or more optical systems and sensors, optionally including autofocus and zoom features as needed, to capture skin images from a remote distance for covering entire skin regions, from a short distance for taking a close-up high resolution image of a selected skin lesion, and for continuously tracking a selected skin lesion while the handheld inspection device is moved toward the skin for ensuring the identity of the selected skin lesion whose close-up image is taken. Skin lesion database 124A stores past inspection results of selected skin lesions and records the results of the current inspection—see also FIG. 3 below. While video camera 128 acts as a sensor for capturing high resolution images of a selected skin lesion, other sensors 132 are optionally included and operated, for acquiring additional information of the selected skin lesion, as known in the art of digital dermatoscopy, and may include, for example, an infrared camera, a thermal camera, and/or a three dimensional stereo camera. While conventional room lighting may be sometimes sufficient for the operation of video camera 128, illuminator 136 is optionally added for illuminating the skin region, and specifically the target skin lesion, serving video camera 128 and optionally other sensors 132, while providing light wavelengths as appropriate for the operation of video camera 128 and other sensors 132.

Laser 140 is optionally included in handheld inspection device 104A as a component or attachment, to project at least one laser beam within or in proximity to the target skin lesion, for at least one of: visually identifying the selected skin lesion on the skin surface, which may aid the user in the course of moving the handheld inspection device toward the selected skin lesion during the inspection operation; measuring the distance between the handheld inspection device and the skin surface; or measuring the angle between the handheld inspection device's optical axis and the skin surface. The use of laser 140 will be further elaborated with references to FIGS. 5B-C and 6B-C below. Other functions 144 may include unrelated functions, such as navigation, personal communication or games, especially if handheld inspection device 104A use the platform of a multipurpose handheld device, such as a cellular phone, programmed to perform the functions of a handheld inspection device depicted in the present disclosure, and to which, optionally, illuminator 136, other sensors 132 and/or laser 140 may be attached. Communication device 142, such as a cellular or Wi-Fi link, is optionally used to send inspection results to a clinic, and/or to receive inspection instructions and guidance from a clinic. Power supply 114, such as a rechargeable battery, energizes the other components of handheld inspection device 104A.

It will be noted that illuminator 136 and/or laser 140 can be considered as elements of user interface 110A, if they serve to provide a user with useful information, such as identifying a skin lesion by a laser beam, interpreting a light flash as signaling the completion of a certain skin lesion inspection, or turning off a laser beam to signal that a target skin lesion has been lost during the motion of the handheld inspection device toward the skin surface. Also, video camera 128 can be considered an element of user interface 110A, for example when it is used to acquire user selectable images.

A standalone handheld inspection device may sometimes be inadequate or inconvenient for self-operation by the patient, where either certain skin regions are hard to reach by handheld inspection device 104A, or screen 116A is hard to watch by the patient when video camera 128 is aimed at a certain skin region, for example, the patient's face or head. However, the standalone handheld inspection device 104A may be fully operative when operated by a user that is other than the patient, such as a family member, or when there is a need to inspect only specific skin regions, such as the front side of the patient's hip, that are convenient to approach with the handheld inspection device 104A while watching screen 116A.

A System of a Handheld Inspection Device and a Computer

Figure 1B:
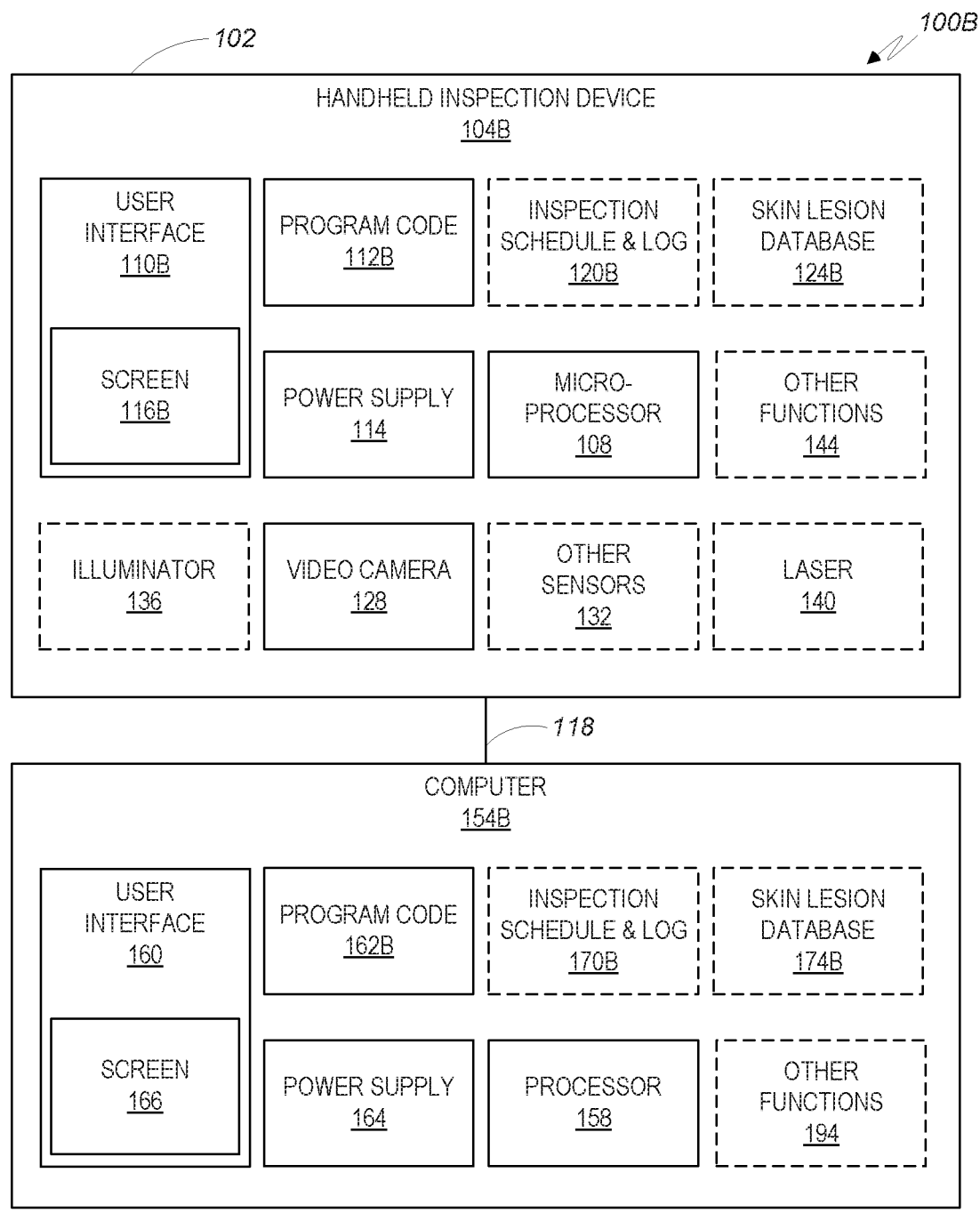

FIG. 1B describes system 100B, wherein handheld inspection device 104B communicates with a local computer 154B during operation, so that some functions of handheld inspection device 104A of FIG. 1A are moved to, or shared with computer 154B. Computer 154B, such as a desktop, laptop or tablet computer, is positioned next to the user that operates handheld inspection device 104B, and communicates with handheld inspection device 104B via short-range communication link 118, such as a wired, Bluetooth or Wi-Fi link.

Handheld inspection device 104B is similar to handheld inspection device 104A of FIG. 1A, except that, based on design practices, performance and user convenience considerations, some functions, operations and data are now shared between handheld inspection device 104B and computer 154B, or entirely moved to computer 154B. For example, the functions implemented by program code 112A of FIG. 1A may now be shared between program code 112B and program code 162B, and, accordingly, some of the functions run by microprocessor 108 of standalone handheld inspection device 104A may now be moved to computer processor 158 of computer 154B, such functions being, for example, user guidance and database access. Inspection schedule & log 120A and skin lesion database 124A of FIG. 1A may now be shared between inspection schedule & log 120B and inspection schedule & log 170B, and between skin lesion database 124B and skin lesion database 174B, or may entirely be moved to inspection schedule & log 170B and skin lesion database 174B, respectively. User interface 110B, and specifically screen 116B, may now be minimal, with operational and user guidance functionalities optionally moved to user interface 160 and screen 166, respectively. It will be noted the sharing data between two or more devices may include having redundant copies of part or all of the data, for backup or operational considerations.

The configuration of FIG. 1B allows a user to conveniently watch the larger screen 166 of computer 154B, while maneuvering handheld inspection device 104B to view and approach a selected skin region. It may be operated by the patient or by a user other than the patient.

A System of a Handheld Inspection Device, a Computer and a Server

Figure 1C:
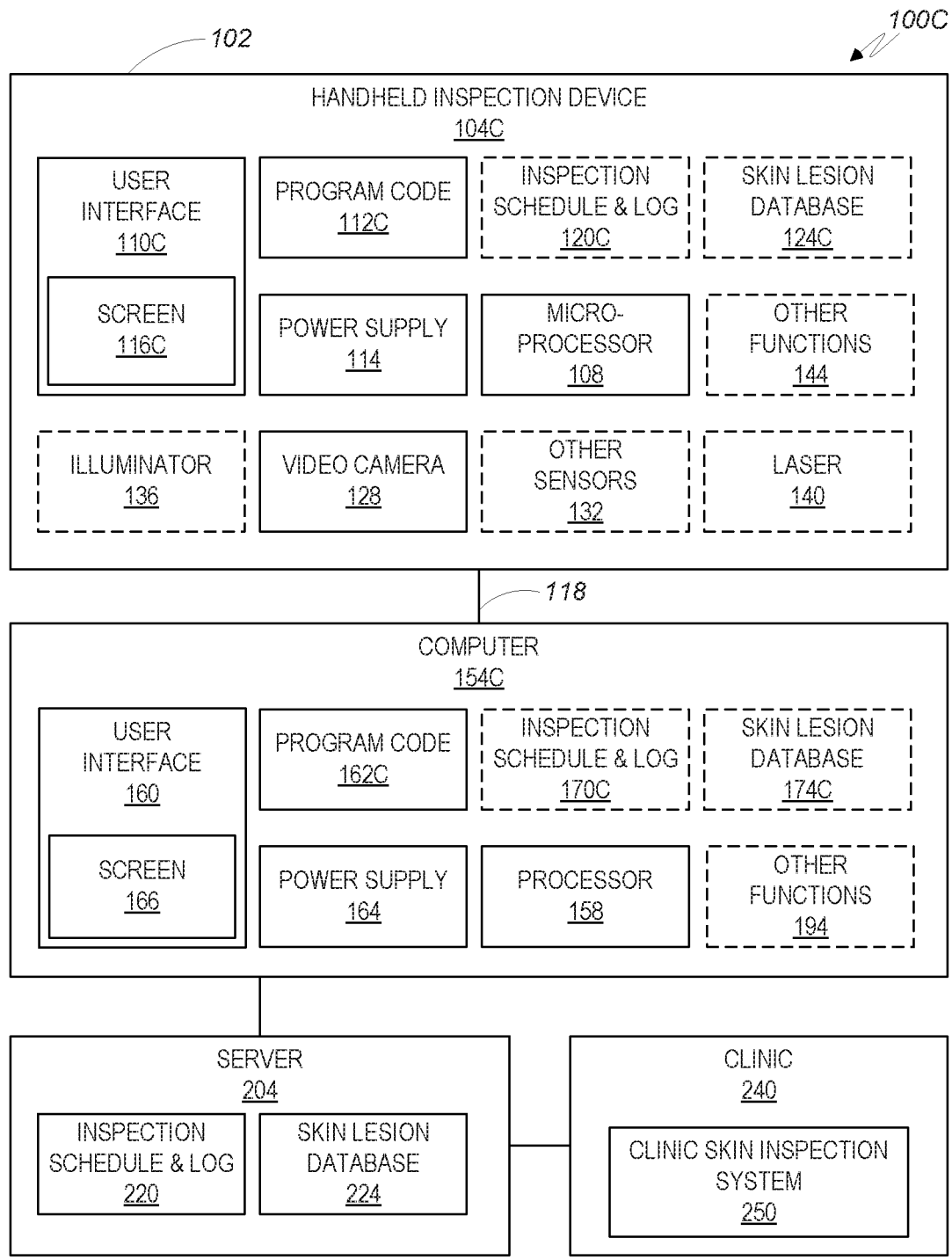

FIG. 1C depicts system 100C, in which server 204 is added, to host all or part of the contents of inspection schedule & log 120A and skin lesion database 124A of FIG. 1A. Accordingly, according to design and operational considerations, now all or part of the contents of inspection schedule & log 120A and skin lesion database 124A of FIG. 1A may be copied or entirely moved to inspection schedule & log 220 and skin lesion database 224 of server 204, or shared among inspection schedule & log 120C, inspection schedule & log 170C, inspection schedule & log 220, skin lesion database 124C, skin lesion database 174C and skin lesion database 224.

Server 204, such as a server of a clinic, a health insurance company, or a national health organization, preferably communicates with computer 154C via a network, such as the Internet or cellular network, for maintaining updated inspection schedule & log 220 and skin lesion database 224, for both backup and for access to inspection plans and results by qualified personnel at clinic 240. Thus, a dermatologist can use a computer at clinic 240 to monitor skin inspection results reported by handheld inspection device 104C and/or computer 154C to server 204, can update inspection schedule & log 220 for requiring additional inspection of suspect skin lesions, or can use clinic skin inspection system 250 for initially establishing skin lesion database 224 and identifying the selected skin lesions for periodic inspection, as well as for integrating inspection data taken by clinic skin inspection system 250 during visits to clinic 240, along with inspection data from handheld inspection device 104C, into skin lesion database 224.

A System of a Handheld Inspection Device and a Server

Figure 1D:
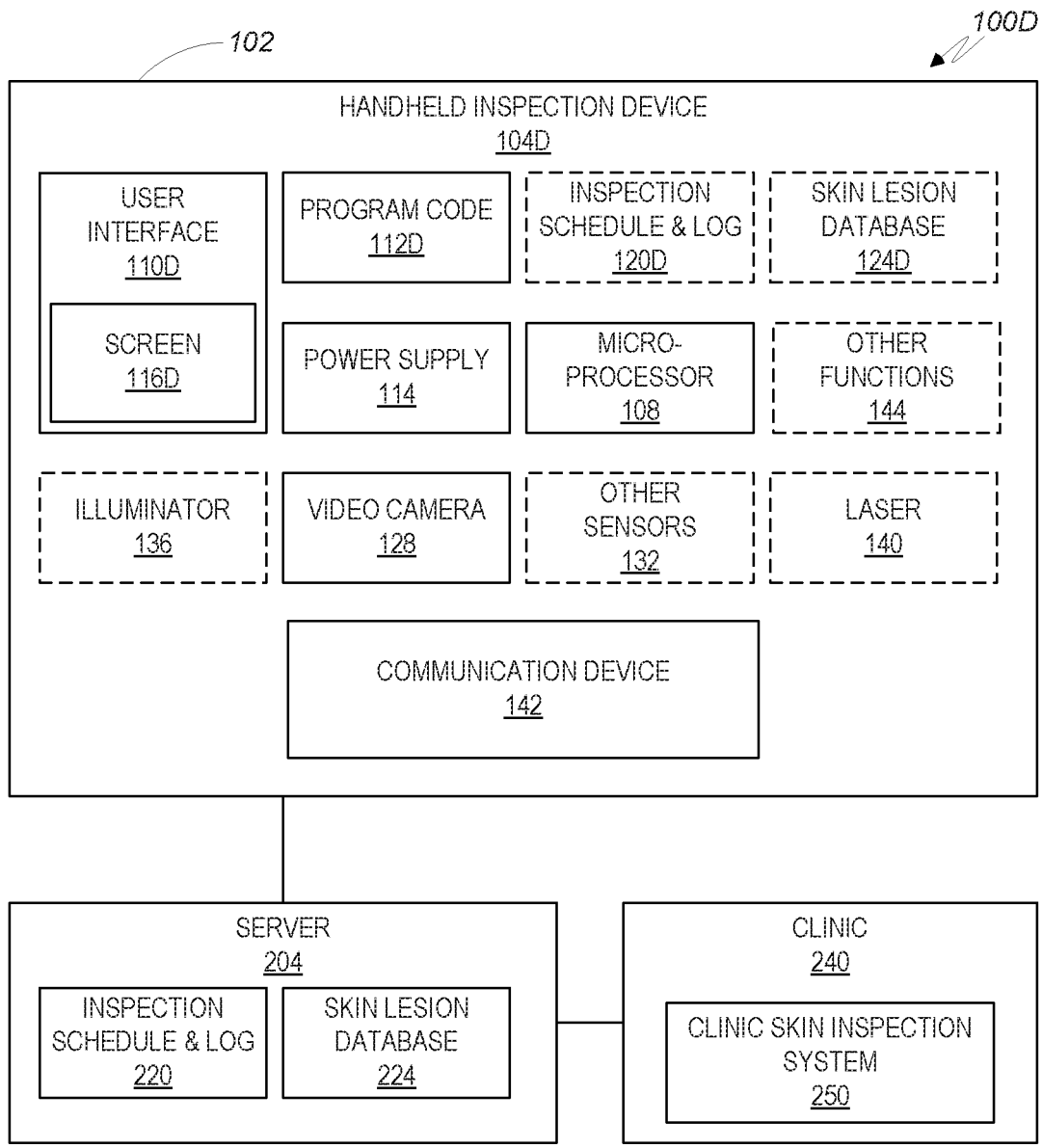

FIG. 1D describes system 100D, in which handheld inspection device 104D communicates, using communication device 142 and a communication link, such as a cellular or Wi-Fi link, with server 204, which further communicates with clinic skin inspection system 250. In system 100D, the contents of inspection schedule & log 120A and skin lesion database 124A of FIG. 1A are copied, moved to or shared with inspection schedule & log 220 and skin lesion database 224, respectively, and data is exchanged, both ways, between server 204 and clinic 240, offering some of the services and advantages described above with reference to FIG. 1C.

Dividing the Body Skin Surface into Regions

For efficient and convenient operation of the process described in the present disclosure, the skin area is preferably divided into skin regions. A skin region is a part of the skin surface that: (a) can be clearly defined to a user by words and/or graphic illustration; (b) an image of the region can be conveniently acquired by a user using the handheld inspection device of the present disclosure; and (c) the region contains sufficient visual features to allow computer vision implemented in the system of the present disclosure to recognize the region and map the skin lesions within the region. Visual features may include limb/body contours, fingers, nails, facial features and breast, as demonstrated, for example, by the article in http://files.is.tue.mpg.de/black/papers/sidWorkshop04.pdf (Ref-1), which is incorporated herein by reference.

Figure 2A:
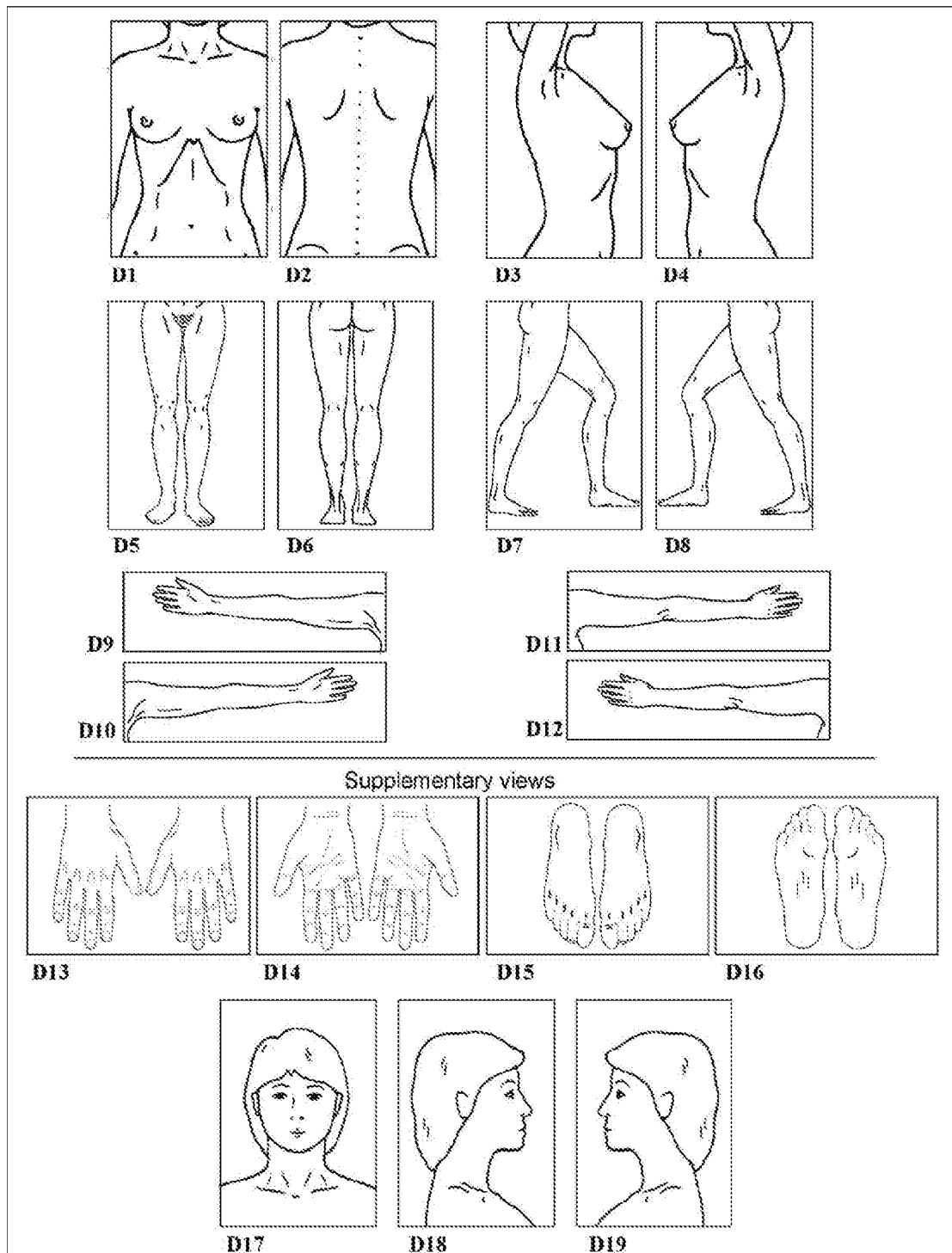

As an example, FIGS. 2A and 2B describe, by illustrations and text, respectively, a standard division of a skin surface into nineteen views, as published by the UK Institute of Medical Illustrators in their *IMI National Guidelines: Guide to Good Practice: Mole Mapping* of February 2013. The nineteen views of FIGS. 2A and 2B may adequately define regions to be used for skin inspection under the present disclosure, if the handheld inspection device is operated by a user who is other than the patient. For self examination by the patient, a subdivision of IMI views into smaller regions may be required or advantageous; for example: view D14 of FIG. 2A that shows both palms, may preferably be divided into two regions: "left palm" and "right palm", to allow the user to hold the handheld inspection device with one hand while inspecting the other palm. Another consideration to determine the preferred size of a specific region in self-examination by a patient is the optical design of video camera 128, that needs to cover the entire region from a distance that is conveniently reachable by the patient's hand holding the handheld inspection device. Also, it is important that a skin region contains sufficient visual features to allow image processing to identify the skin region and map the included skin lesions. These features should remain identifiable under ordinary illumination, scaling and position changes, and be distinctive to separate them from the background and clutter of similar features. A representative method is described in US Patent US2009028442, which is incorporated herein by reference.

Figure 9:
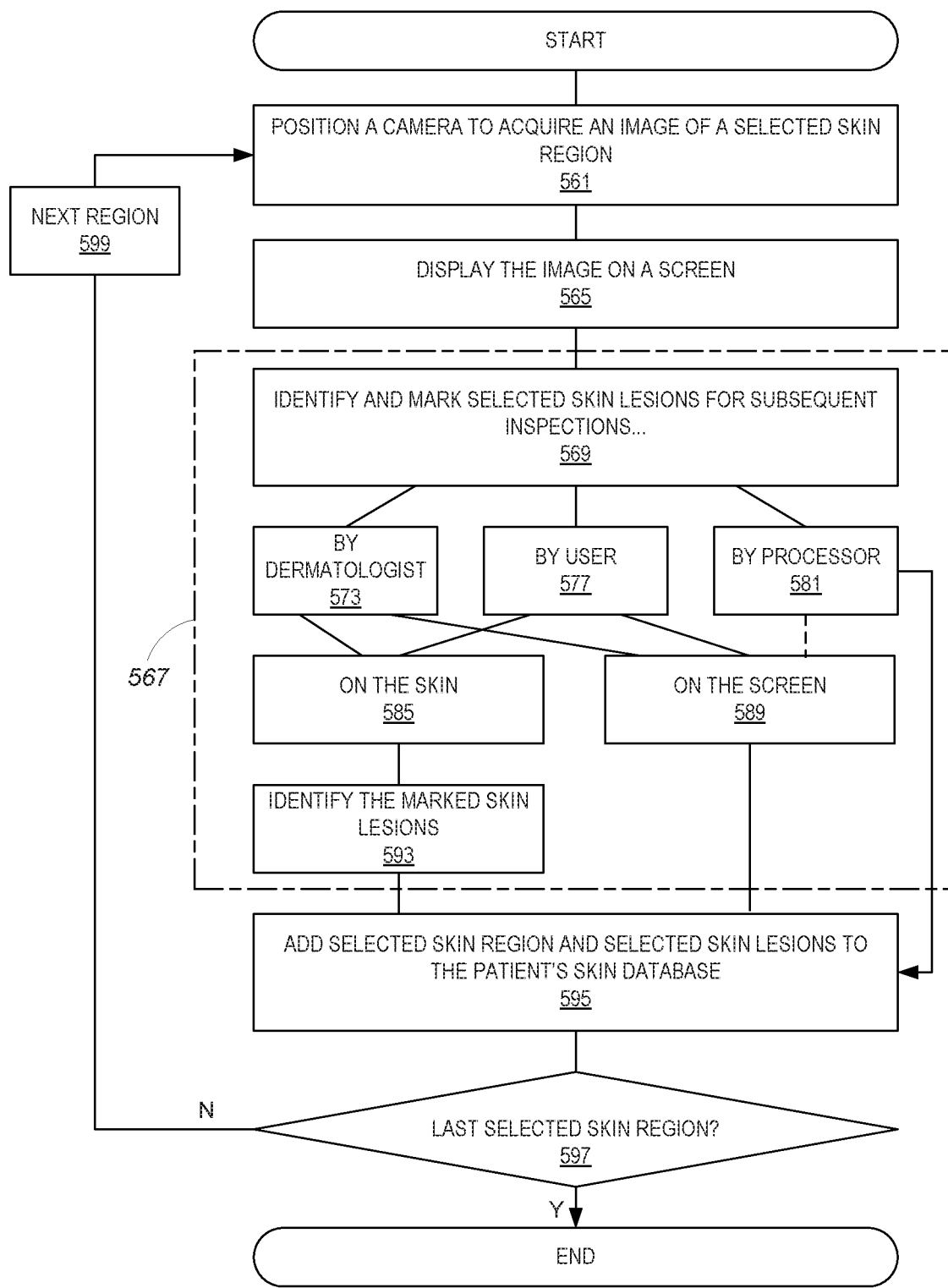
FIG. 9 is a flowchart schematically describing a process for establishing a new skin database for a patient.

It will be noted that even if the number of regions is relatively large, a routine periodic inspection may involve only a few selected regions, that contain the few selected skin lesions selected for routine periodic self-inspection by a dermatologist, a user or a processor (see FIG. 9).

A specific division of the skin surface into regions is a matter of design preferences, and is out of the scope of the present disclosure. The following description assumes that the skin surface is divided into regions, and each region is identifiable to a user by text and/or a graphic illustrations, so that the user can be directed to examine a skin region selected by a processor.

Patient's Skin Database

The present disclosure focuses on periodic inspection of the skin of one patient. Accordingly, the following description focuses on managing skin data related to that one person.

Figure 3:
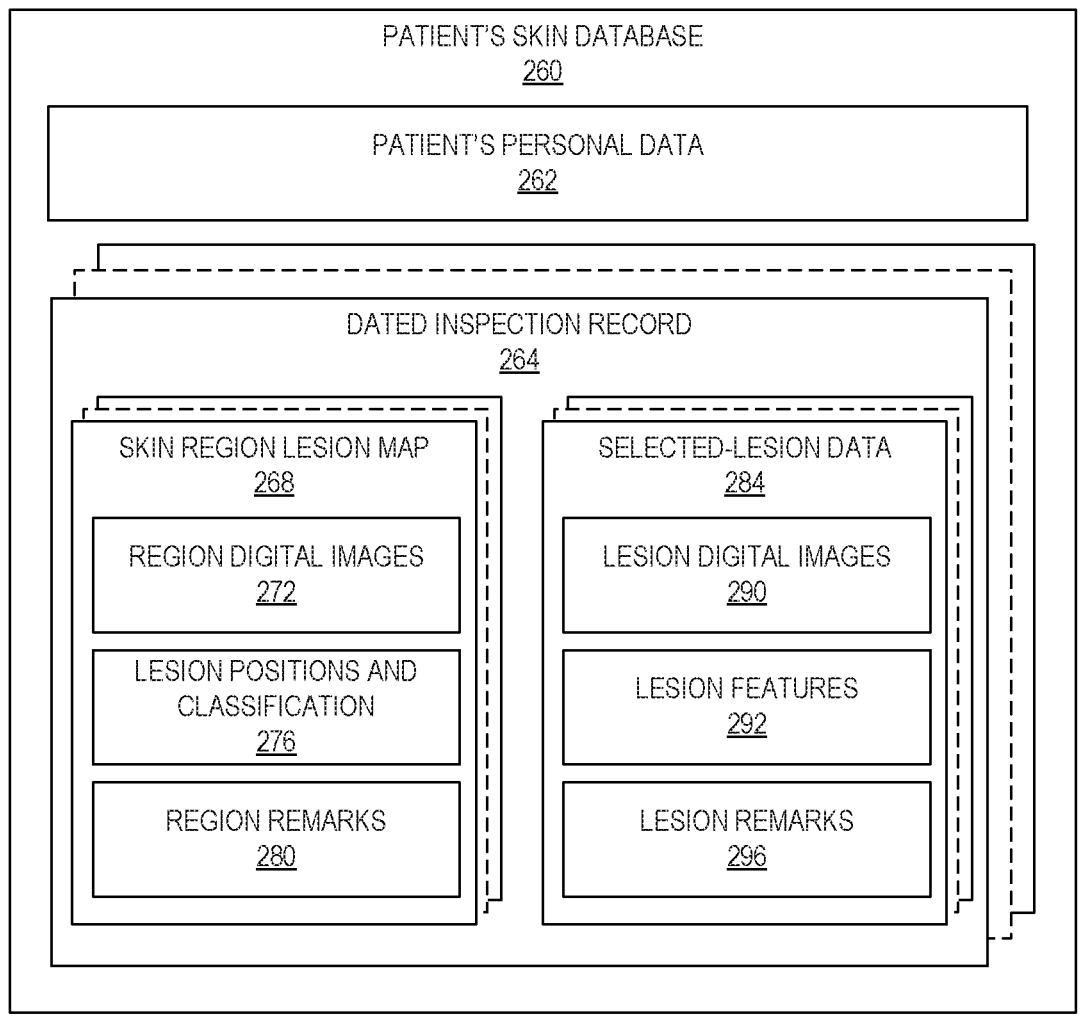
FIG. 3 is a block diagram describing a skin database of a patient.

FIG. 3 schematically describes a patient's skin database 260, that stores and maintains data that relates to the skin of a patient. According to the implementations of systems 100A-D of FIGS. 1A-D above, database 260 is implemented as skin lesion database 124A of FIG. 1A, or is shared between skin lesion database 124B and skin lesion database 174B of FIG. 1B, or is shared among skin lesion database 124C, skin lesion database 174C and skin lesion database 224 of FIG. 1C, or is shared between skin lesion database 124B and skin lesion database 224 of FIG. 1D, as depicted above with references to FIGS. 1A-1D. As already noted above, shared data may have redundant copies in more than one device of the above. As an example, in user interface 110C of FIG. 1C, skin lesion database 224 may include all skin lesions of the patient, skin lesion database 174C may include just the skin lesions selected for periodic inspection, while skin lesion database 124C may include just the skin lesions assigned for the current inspection session.

Patient's personal data 262 is a record including customary personal data that identify the customer, such as name, address and contact details, and serve to associate the skin data with the patient.

The pertinent skin data of the patient is preferably organized in a plurality of dated inspection records 264, each representing a snapshot of the patient's skin status at a certain date in which the skin has been or is being inspected, either by a handheld inspection device of the present disclosure, or, in the configurations of FIGS. 1C and 1D, inspection may also be made at a clinic and its results integrated into patient's skin database 260. The contents of dated inspection record 264 may be roughly divided into skin lesion digital images 288 that include data that pertains to skin regions, and selected skin lesion data 284 that pertains to specific skin lesions selected for inspection. Skin region lesion map 268 includes region digital images 272 that document one or more snapshots of the skin region taken at the date of the inspection, and preferably also lesion positions and classification 276, which maps the lesions within the region, each with its position and classification. The classification may include, for example, whether a specific lesion is selected for periodic examination, and optionally also the frequency of examination, such as every three months or once a year. The data in lesion positions and classification 276 is determined either manually by a qualified professional, or automatically by using image processing and digital dermatology technology, or the combination of both. Region remarks 280 are optionally added by a dermatologist or technician, to include medical or technical aspects related to the examination procedure, for example, special lighting requirements, or the need to request assistance from a user other than the patient.

Selected skin lesion data 284 includes that data acquired, for a specific selected skin lesion, during examination on the date of creation of dated inspection record 264. Skin lesion digital images 290 includes one or more close-up images of the selected skin lesion, which may also include, according to the technologies implemented in other sensors 132 of FIGS. 1A-D, also infrared images, 3D images, thermal images and/or any other images captured by other sensors 132. Skin lesion features 292, such as dimensions, borders, colors, and any other lesion parameters known in the art of digital dermatology, are optionally extracted from skin lesion digital images 290, either automatically by image processing using techniques that employ invariant feature selection, active contours, different segmentation techniques and pre-trained classifiers, according to the latest computer vision techniques, and/or manually by a dermatologist; see also, for example: http://www.mathworks.com/matlabcentral/answers/uploaded_files/6099/another %20paper.pdf (Ref-2), which is incorporated herein by reference. Skin lesion remarks 296 are optionally added by a dermatologist, for example to call for a specific action or attention with respect to the selected skin lesion.

Identification of a Selected Skin Lesion within a Region

Figure 4A:
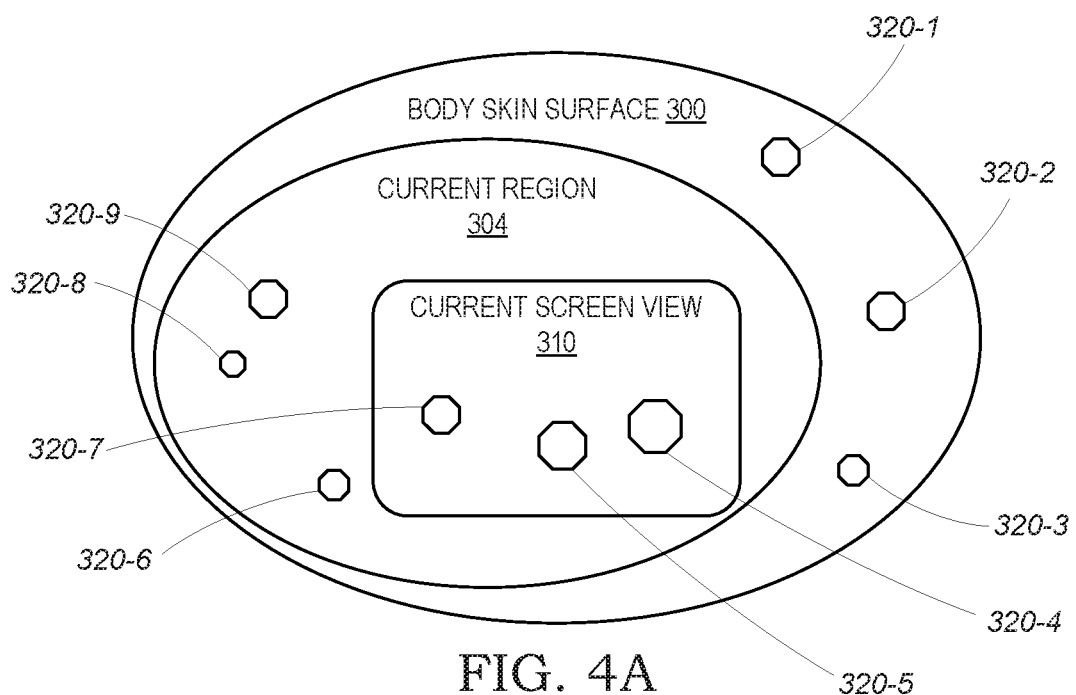
FIGS. 4A-4C are schematic illustrations describing how a selected skin lesion is identified during inspection.
Figure 4B:
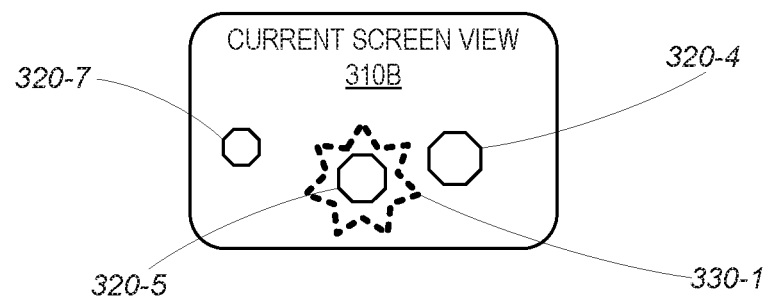
Figure 4C:
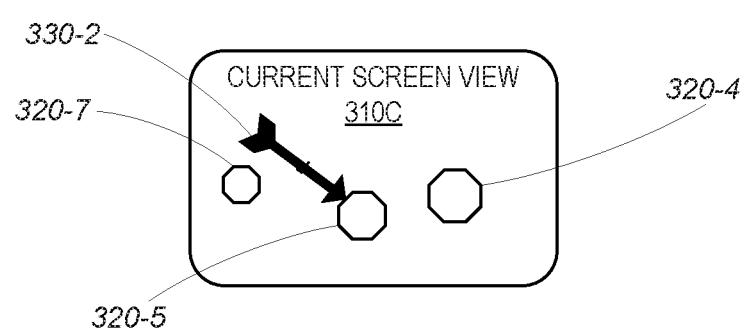

FIGS. 4A-4C schematically describe how a selected skin lesion is identified during the inspection process of the present disclosure.

Starting with FIG. 4A, body skin surface 300 is the entire skin surface of the patient, which includes a plurality of skin lesions symbolically represented by skin lesion 320-1 to skin lesion 320-9. The number of the skin lesions of a patient may be any number, with 9 being just an arbitrary number for demonstration purpose only within the context of FIGS. 4A-4C. Current region 304 represent the skin region currently inspected, such as the front part of the left hip, and contains skin lesions 320-4 to 320-9. Current screen view 310 shows the current skin image taken by video camera 128 and seen, for example, on screen 116A of FIG. 1A or screen 116B and/or screen 166 of FIG. 1B, or their equivalents in FIGS. 1C-1D. Initially in the inspection process of current region 304, current screen view 310 encompasses the entire current region 304 and therefore shows all its skin lesions 320-4 to 320-9. The current screen view 310 of FIG. 4A demonstrates a snapshot taken during the travel of the handheld inspection device toward the skin, where the field of view of video camera 128 narrows, to capture only a subset of the skin lesions of the current region 304, illustrated by skin lesion 320-4, skin lesion 320-5 and skin lesion 320-7.

FIG. 4B shows the snapshot of current screen view 310, where a marker 330-1 is displayed on the screen to identify the target skin lesion to be examined—skin lesion 320-5 in the present example. The marker is generated by microprocessor 108 or computer processor 158, to highlight target skin lesion 320-5 and distinguish it from the other skin lesions currently displayed on the screen, in order to aid the user in aiming the handheld inspection device toward the target skin lesion 320-5. FIG. 4C demonstrates an alternative graphic design of marker 330-2, that serves the same purpose as marker 330-1 of FIG. 4B.

Reaching a Position for Close-Up Inspection

Close-up inspection can be made when the handheld inspection device is positioned close enough to the skin surface for acquiring sufficient detail by video camera 128 and optionally also by other sensors 132 and illuminator 136, all of which depending on specific qualities of the respective components, and on operational requirements defining the level of detail sufficient for close-up inspection. In one extreme, all such parameters can be transformed by a designer into a simple parameter such as the distance from the skin, for example "15-20 cm from the skin"; on the other extreme, each of the video camera 128 and other sensors 132 dynamically and continually examines the quality and level of detail acquired by the respective sensor, and when a predefined threshold is reached for all sensors, the close-up inspection is concluded and the user is notified via the user interface of the handheld inspection device or the computer. A combination of distance and sensor data reaching a predefined threshold is also possible.

Figure 5A:
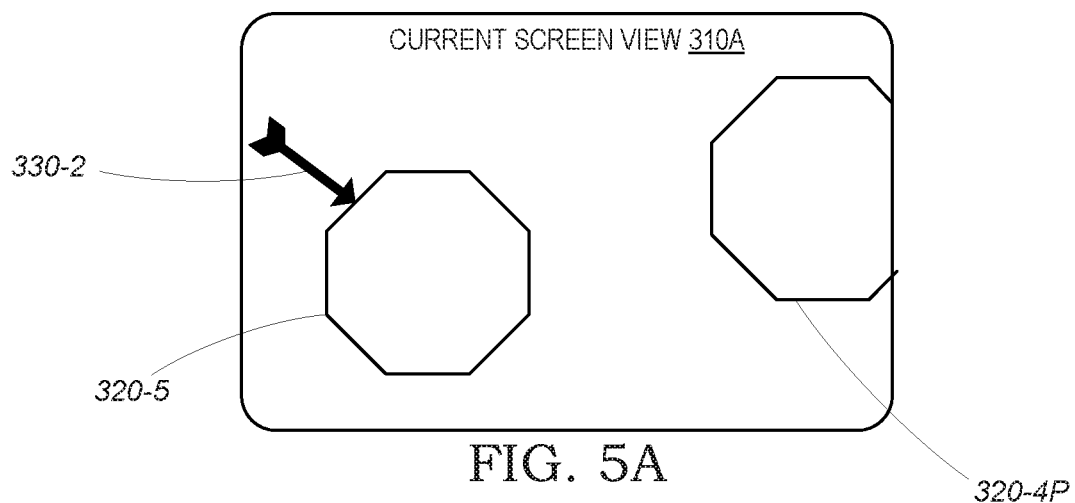
FIGS. 5A-5C and 6A-6C are schematic illustrations depicting the optional use of a laser for pointing and/or measurement.

It will be noted that when reaching a position for close-up inspection, the current screen view may include just the target skin lesion, or it may include also other neighboring skin lesions, in whole or in part, as demonstrated by part of a skin lesion 320-4P shown in FIG. 5A.

Laser-Assisted Inspection

Figure 5B:
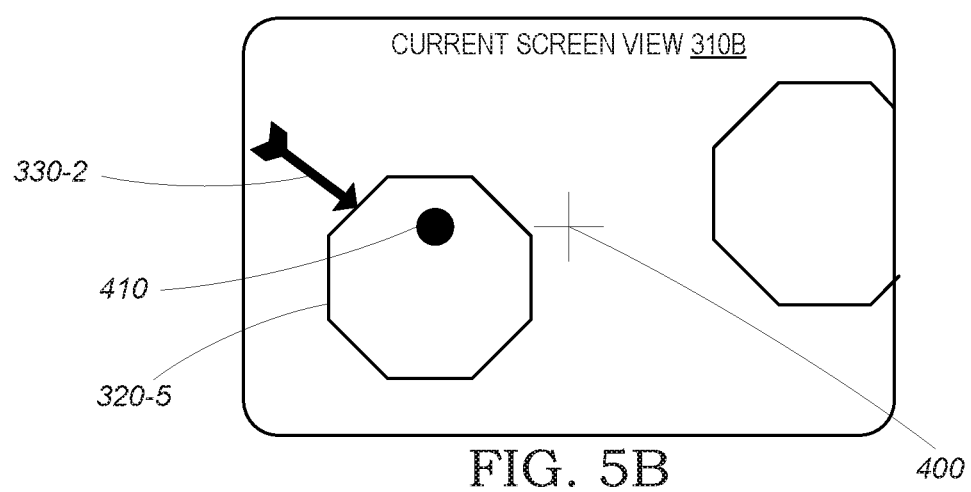
Figure 5C:
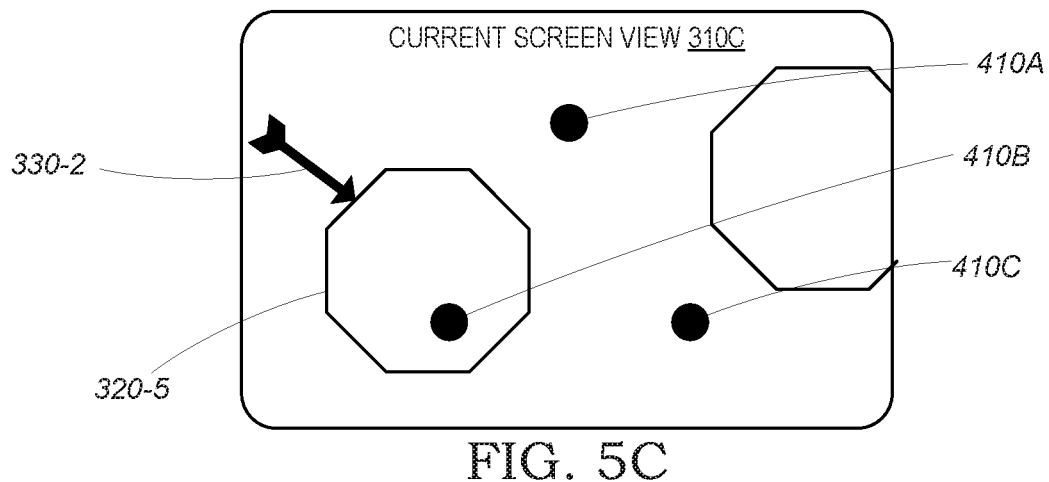
Figure 6A:
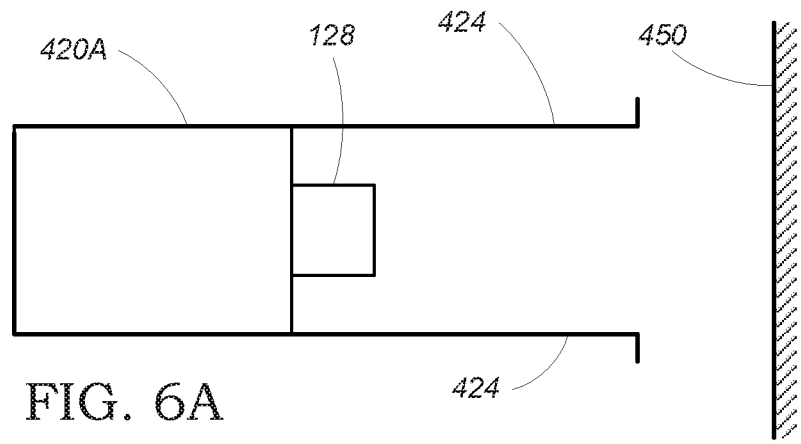

FIGS. 5A-5C and 6A-6C schematically illustrate the optional use of laser 140 that may be included in the handheld inspection device of FIGS. 1A-1D. FIG. 5A shows a close-up view of target skin lesion 320-5 marked by marker 330-2 within current screen view 310A, with no laser 140 operating in the handheld inspection device and no laser spot present. While the close-up image may be sufficient for extracting shape, border and color features of target skin lesion 320-5, the size of target skin lesion 320-5 is hard to measure, since it depends on the position of video camera 128 relatively to the target skin lesion. Use of a mechanical stopper 424, such as a transparent ring extending from handheld inspection device 420A in front of video camera 128, as demonstrated by FIG. 6A, provides the missing information and allows to calculate the dimensions of target skin lesion 320-5 from the known length of mechanical stopper 424. Use of mechanical stopper 424 may also assist the user in positioning video camera 128 perpendicularly to skin surface 450.

Figure 6B:
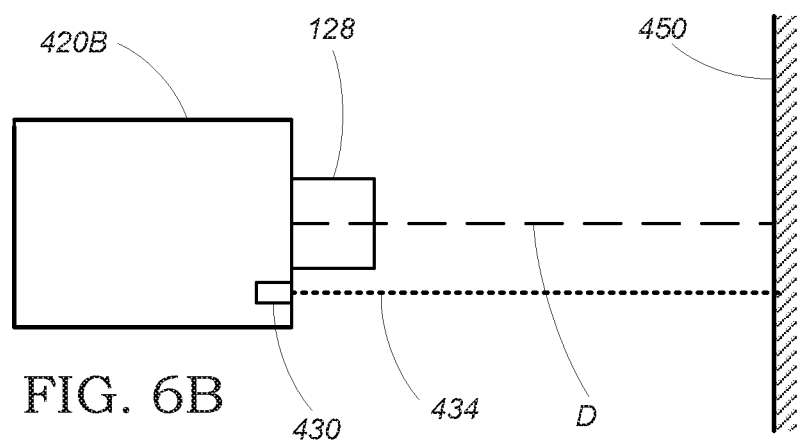

FIGS. 5B and 6B demonstrate the use of a single laser beam for measuring the dimensions of target skin lesion 320-5 without touching the skin surface 450. Thus, laser source 430 is included in handheld inspection device 420B to produce a laser beam 434 that is parallel to and is in known distance from optical axis 440 of video camera 128. Laser beam 434 produces a visible laser dot 410 within or in close proximity to target skin lesion 320-5. Since the distance between the image center 400 and laser dot 410 is the same as the known distance between laser beam 434 and optical axis 440, the available scale information is sufficient to determine the dimensions of target skin lesion 320-5, trusting that the user properly positions the camera perpendicularly to skin surface 450.

Figure 6C:
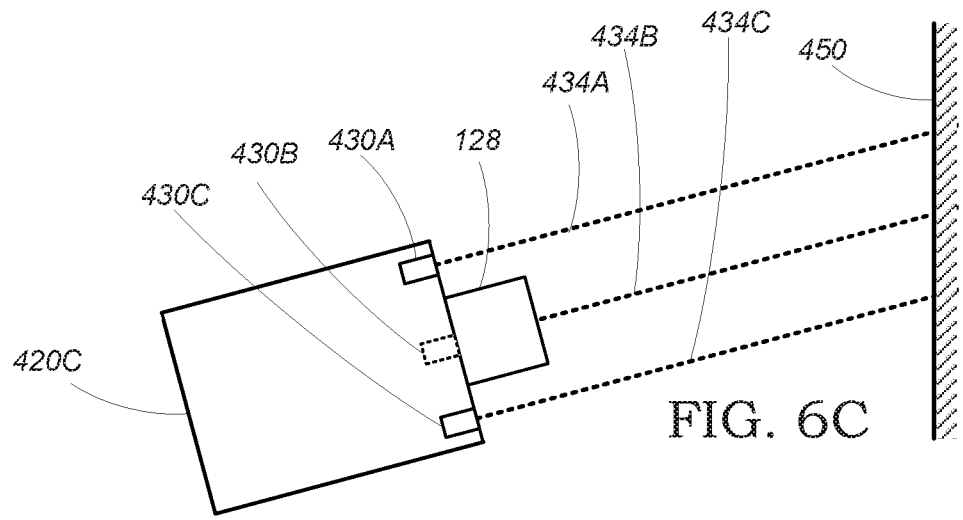

FIGS. 5C and 6C demonstrate the use of three parallel laser beams, preferably arranged as the corners of an equilateral triangle around the optical axis of video camera 128 of handheld inspection device 420C. Thus laser source 430A, laser source 430B and laser source 430C project laser beam 434A, laser beam 434B and laser beam 434C, respectively, and current screen view 310C shows the respective laser dot 410A, laser dot 410B and laser dot 410C. Since the distances among the laser dots of FIG. 5C are the same as the known distances among the laser sources of FIG. 6C, the dimensions of skin lesion 320-5 can be easily calculated. Furthermore, in the case that video camera 128 is not perpendicular to skin surface 450, as illustrated in FIG. 6C, the three respective laser dots will deviate from forming the corners of an equilateral triangle, and the actual distances among the dots can then still serve for calculating the dimensions of skin lesion 320-5 even when the image is taken from a reasonably-inclined camera, as taught, for example, by the book *Multiple View Geometry in Computer Vision*, Second Edition, by Richard Hartley and Andrew Zisserman, Cambridge University Press, March 2004, incorporated herein by reference.

Another benefit from using a laser as in FIGS. 6B-6C, is that the laser beam or beams serve as a laser pointer that highlights the target skin lesion on the skin surface. This may make the process of manually approaching the skin surface with a handheld inspection device of the present disclosure more convenient, efficient and accurate.

It will be appreciated that arrangements of laser beams other than those depicted in FIGS. 6B-6C above, can be applied for achieving similar results of measurement and/or pointing.

Image Acquisition by the Video Camera

Video camera 128 acquires images in the course of the inspection process of the present disclosure for two purposes: (1) in order to guide the user toward the target skin lesion; and (2) for capturing a close-up image of the target skin lesion.

Figure 7:
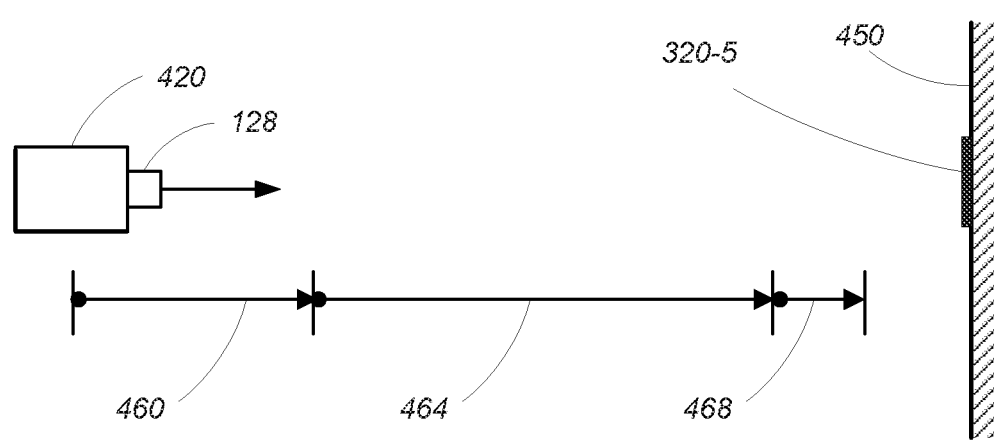
FIG. 7 is a schematic illustration depicting the travel of a handheld inspection device toward a selected lesion.

FIG. 7 schematically illustrates the travel of a handheld inspection device such as the one of FIGS. 1A-1D, from a distance toward skin surface 450, until making a close-up inspection at a suitable position relative to the target skin lesion 320-5.

Initially, the user is instructed via screen 116A or screen 166, by text instructions and/or graphic illustrations, to position the handheld inspection device 420 remotely from and aimed at the current selected skin region, so that the video camera 128 captures all or a sufficient part of the current selected skin region. As an example, the user may be instructed, by text and illustrations: "place the device two feet from the front face of your left hip, so that you can see the entire hip on the screen". Technically, an adequate position within the region mapping range 460 allows viewing both the current target skin lesion 320-5, and sufficient visual features within the current skin region, to allow image processing to map the elements viewed on the screen and positively identify the target skin lesion 320-5 within the current screen view, so that it can be marked as demonstrated in FIG. 4B or 4C above.

It is presumed that region mapping range 460 is too distant from skin surface 450 for making a quality close-up inspection, and therefore, once the current screen view shows and marks the current target skin lesion, the user is instructed, for example by text on a screen, to move the handheld inspection device toward the target skin lesion. Such instruction can be easily followed by users accustomed to operate pointing devices, such as a mouse, and can be further assisted by a laser beam that is pointing at the selected lesion, for example, if the configuration of FIG. 6B or 6C is implemented. During the travel of handheld inspection device 420 toward the skin surface 450, while the video camera 128 is within the tracking range 464, the field of view of the camera gradually narrows, showing less and less area of the current skin region, and the target skin lesion appears larger and larger while it is continuously tracked and marked on the screen, for two purposes: (1) ensuring that the final close-up inspection will take data of the target skin lesion and not of a neighbor skin lesion; and (2) properly guiding the user toward the target skin lesion. If, during the travel within tracking range 464 the image of the current target skin lesion is lost, the process may be interrupted, and the user is preferably instructed to pull the handheld inspection device 420 away from the skin, and repeat the process above for the same target skin lesion.

Once handheld inspection device 420 successfully passes tracking range 464 without losing the target skin lesion, it reaches a close-up inspection range 468 that is suitable for making the close-up inspection. The close-up inspection is preferably made automatically, upon detecting that the camera is within the close-up inspection range 468, while providing the user with an indication, for example by text, light flash, sound and/or vibration, that the current inspection has been successfully completed, and the user is then possibly instructed to repeat the process for another target skin lesion within the current region, or to move to another region that includes other selected skin lesions for inspection.

It will be appreciated that region mapping range 460 and the beginning of tracking range 464 can be defined qualitatively, according to the size and shape of the region (for example, at least 90% of the visualized region must fit into camera field of view) and actual deployment of visual features that are sufficient for computerized mapping of the skin lesions within the region.

Close-up inspection range 468 depends on the characteristics of video camera 128, illuminator 136 and other sensors 132 that are optionally involved in additional inspection technologies implemented in handheld inspection device 420 beyond a close-up image taken by video camera 128. It will also be appreciated that, in case of using a mechanical stopper, as depicted in FIG. 6A, close-up inspection range 468 may become a fixed number determined by the length of the mechanical stopper 424.

Inspection Process

Figure 8:
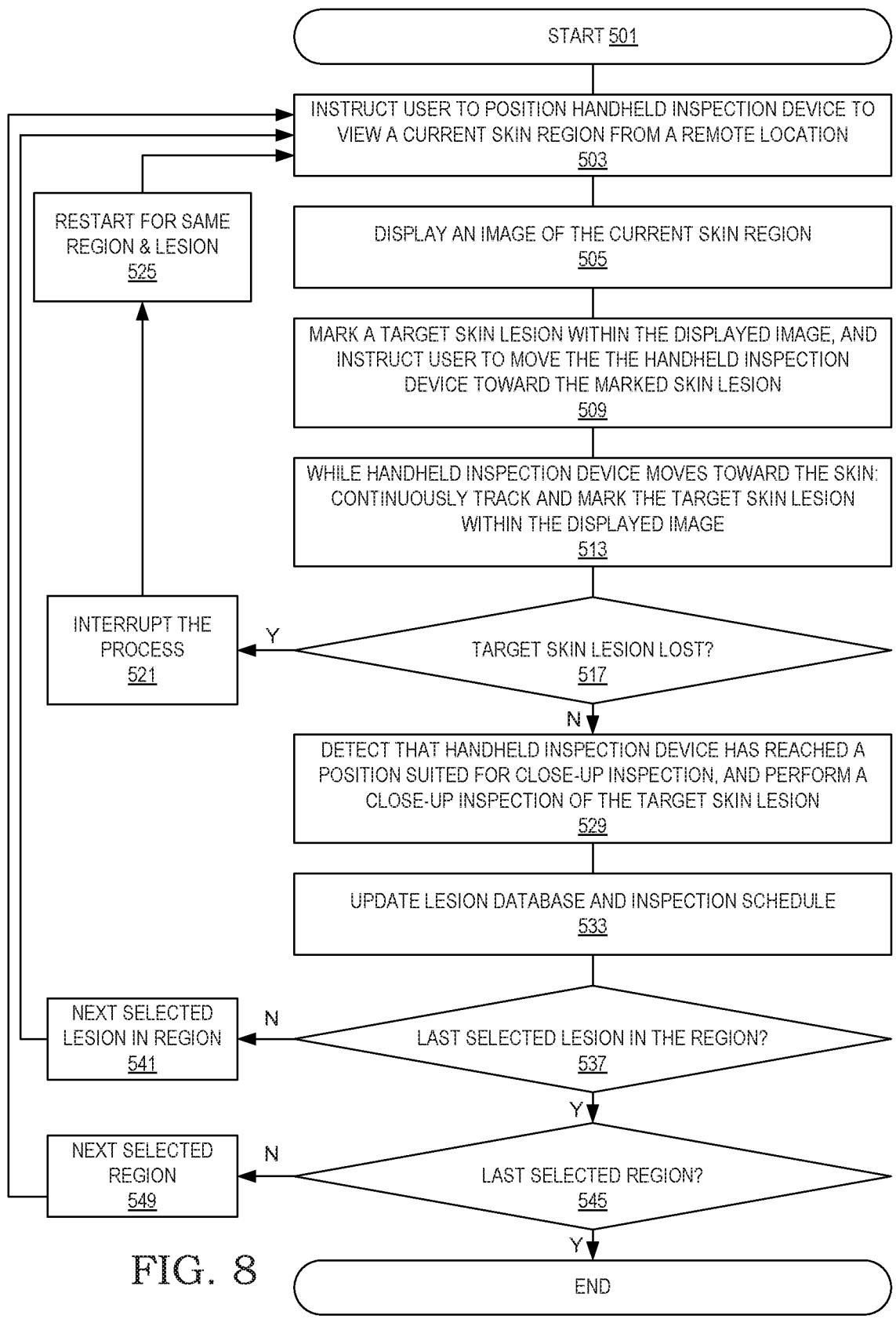
FIG. 8 is a flowchart that depicts a process of close-up inspection using a system of the present disclosure.

FIG. 8 depicts a process of close-up inspection using a system of the present disclosure, such as any of system 100A of FIG. 1A, system 100B of FIG. 1B, system 100C of FIG. 1C, or system 100D of FIG. 1D. The process below concerns close-up inspection of selected skin lesions of a certain patient, carried out by a user, who may be the patient and/or another person assisting the patient, operating a handheld inspection device such as 104A-104D of FIGS. 1A-1D, respectively. A selected skin lesion is a skin lesion of the patient that has been preselected for inspection, by a dermatologist or the patient or automatically according to predefined criteria (see FIG. 9), and is identified as a selected skin lesion in the inspection schedule & log and/or in the skin lesion database that are maintained in any of the embodiments depicted in FIGS. 1A-1D. A target skin lesion is a selected skin lesion that is currently inspected by the process of FIG. 8. A current skin region is the skin region that contains the target skin lesion. A processor is any of microprocessor 108 of the handheld inspection device, or computer processor 158 of the computer, or a cooperation between the two.

At the starting point 501 of the process of FIG. 8, a list of at least one selected skin lesion designated for inspection has already been retrieved from the inspection schedule & log and/or the skin lesion database, and a target skin lesion has been selected by the processor for the current inspection. In step 503, the user is instructed, via the user interface of a handheld inspection device such as 110A-110D and/or of a computer such as user interface 160, to position the handheld inspection device at a remote distance from a current skin region that includes the target skin lesion, so that the entire current skin region is shown on the screen, as demonstrated by FIGS. 4A-4C and the respective descriptions. Once the handheld inspection device is properly positioned, then, in step 505 the current screen view displayed on the screen of the handheld inspection device and/or the computer, shows the current skin region, including the skin lesions included in the current skin region. In step 509 the processor of the handheld inspection device of FIGS. 1A-1D and/or the processor of the computer of FIG. 1B or 1C, identifies and marks the target skin lesion within the displayed image, and the user is instructed, for example by a message displayed on the screen, to move the handheld inspection device toward the target skin lesion while centering the marked skin lesion within the displayed image. In step 513, while the handheld inspection device is moved by the user toward the skin surface of current skin region, the processor continuously tracks the target skin lesion and marks it on the screen. If a laser 140 is included in the handheld inspection device, one or more laser beams produce visible light spot(s) on or next to the target skin lesion, which may assist the user in conveniently aiming and moving the handheld inspection device toward the target skin lesion. If the user improperly moves or aims the handheld inspection device so that the target skin lesion is lost, or the line of sight between the handheld inspection device and the target skin lesion is obscured for any reason, then in step 517 such loss is detected by the processor, and the process is interrupted in step 521. The user is then notified of the interruption in step 521 by a signal such as a message, audio beep, vibration, and/or the laser beam turned off. Following the interruption in step 521, in step 525 the user is preferably instructed, for example by a message on the screen, to move the handheld inspection device away from the skin region to a remote distance so that the entire current skin region is shown on the screen, and repeat the process for the same target skin lesion within the same current skin region.

Step 529 detects that the handheld inspection device has reached a close distance from the target skin lesion suited for close-up inspection of the target skin lesion. Such detection may be made, for example, by mechanical stopper 424 of FIG. 6A reaching the skin, by laser beams of FIGS. 6A-6B used to determine the handheld inspection device reaching a predefined distance from the skin, or by the image of the target skin lesion occupying a predefined size or percentage of the screen. Step 529 then continues with making a close-up inspection of the target skin lesion, including at least capturing the image of the target skin lesion and optionally extracting features from the captured image, and possibly also acquiring additional features of the target skin lesion by other sensors 132, and the user is preferably notified of the successful close-up inspection of the target skin lesion by a signal, such as a text message, a light flash by illuminator 136, an audio signal and/or a vibration of the handheld inspection device. In step 533 the event and results, such as current images and extracted data, of the close-up inspection of the target skin lesion, are recorded in the inspection schedule & log and/or in the skin lesion database. In step 537 the processor consults the inspection schedule & log and/or the skin lesion database whether there is an additional selected skin lesion to inspect within the current skin region, and, if needed, moves via step 541 to scan the next target skin lesion in step 503. When all selected skin lesions in the current skin region have been inspected, then step 545 and step 549 lead to inspecting the next skin region that contains selected skin lesions, until completing the scanning of all selected skin lesions of the patient.

Relative Motion Between the Camera and the Skin Surface

When a handheld inspection device, such as handheld inspection device 104B, is used, during self-inspection by a patient, for inspecting hard to reach regions, such as the upper region of the back, it can be convenient to place the handheld inspection device 104B on a stable surface or attach it to a tripod, and then move the patient's body relatively to the handheld inspection device so that the inspected region faces and approaches the video camera 128, while the patient watches screen 166 of computer 154B for controlling the body movement so that the selected skin lesion remains within current screen view 310 until reaching the point of close-up inspection. Accordingly, while the language of the description and claims may recite, for clarity, just a device moving toward the body, such language should be interpreted also alternatively as the body moving toward a device, or the body and a device moving toward each other.

Establishing a New Skin Database

The process of FIG. 8 serves to inspect selected skin lesions that are already predetermined in step 501. FIG. 9 schematically describes a process for establishing a new skin database for a patient, including the identification of selected skin lesions to be inspected in subsequent executions of the process of FIG. 8.

The process of FIG. 9 may be carried out at home using the video camera 128 of a handheld inspection device; at a clinic, such as clinic 240 having a clinic skin inspection system 250 of FIG. 1C or FIG. 1D; or in any other place using a suitable camera, screen and a processor that executes the process of FIG. 9.

In step 561, a camera is positioned by an operator, such as the patient, a dermatologist, or any other person trusted by the patient, to acquire an image of a selected skin region. The selected skin region can be either a skin region that includes at least one suspect skin lesion according to the judgment of the operator or an instruction of a dermatologist, or a current skin region within a systematic screening of all skin regions on the patient's skin surface, for example for screening all the skin views of FIG. 2A. In step 565 the image acquired in step 561 is displayed on a screen, such as screen 116A of FIG. 1A, screen 116B of FIG. 1B, a screen of a clinic skin inspection system 250 (not shown) or any other screen connected to a processor that executes the process of FIG. 9. Sub-process 567, that includes one or more of the alternative paths depicted by steps 569-593, executes to identify, within the selected skin region, zero or more selected lesions for subsequent inspection, such as periodic inspection according to FIG. 8. The zero or more selected skin lesions are those that require further inspection according to human or computer judgment, and are preferably selected and identified as follows: in step 569 a process of identifying and marking selected skin lesions commences, where the selection and marking is made by a dermatologist or another qualified expert, possibly using inspection devices of any kind (step 573), by the a user, that can be either the patient or the operator, who worries about specific skin lesions (step 577), or by a processor which applies image processing and predefined visual criteria (region boundary: fractal, smooth, complex shape, pigmentation color, such as described in http://www.amjorthopedics.com/fileadmin/content_pdf/san/scms_pdf/vol27_i1_Diagnosis_of_Skin_Tumors.pdf (Ref-3), which is incorporated herein by reference, to identify some of the skin lesions included in the selected skin region as selected skin lesion that require further inspection (step 581). The marking of selected skin lesions by a human, in either step 573 or step 577, can be made directly on the skin (step 585), for example by using a pen of visually-distinguishable color to manually draw circles around the selected skin lesions, where in step 593 image processing will detect the drawn circles within the image and identify the encircled skin lesions. Alternatively, the marking of selected skin lesions by a human, in either step 573 or step 577, can be made by the operator on the screen (step 589), for example by using a pointing device such as a mouse or trackball, or by tapping on a touchscreen. In case of step 581, where the selected skin lesions are identified by a processor, the processor-selected skin lesions may be marked on the screen in step 589, for providing information to the operator. It will be noted that a plurality of alternative paths within sub-process 567 may be executed; for example, a processor may identify selected skin lesions in step 581 and present them on the screen in step 589, and the a dermatologist or user may manually add additional selected skin lesions not selected by the processor.

In step 595 the outcomes of step 565 and sub-process 567 are added to the patient's skin database, such as patient's skin database 260, including, for example, the details depicted in FIG. 3. Step 597 checks whether all desired selected skin regions have been screened, and, if not, then step 599 leads to repeating the process of steps 561-595 for another selected skin region.

While the invention has been described with respect to a limited number of embodiments, it will be appreciated by persons skilled in the art that the present invention is not limited by what has been particularly shown and described herein. Rather the scope of the present invention includes both combinations and sub-combinations of the various features described herein, as well as variations and modifications which would occur to persons skilled in the art upon reading the specification and which are not in the prior art.

What is claimed is:

1. A system for inspection of at least one skin lesion within a region on a skin surface, the region containing multiple skin lesions, the system comprising (a) a handheld inspection device including a camera, and (b) at least one processing circuitry configured to:
   (i) acquire, using the camera, a current image, the current image including the region;
   (ii) display the image on a screen;
   (iii) mark a target skin lesion of the skin lesions on the image displayed on the screen, to visually distinguish the target skin lesion from other skin lesions within the region, the target skin lesion being selected for close-up inspection;
   (iv) acquire, using the camera, while the handheld inspection device is moved toward the skin surface, a subsequent image, subsequent to the current image, the subsequent image acquired by the camera from a first distance from the target skin lesion, smaller than a second distance from the target skin lesion from which the current image was acquired;
   (v) display the subsequent image on the screen;
   (vi) check presence of the target skin lesion within the subsequent image;
   (vii) upon the target skin lesion being present within the subsequent image, mark the target skin lesion on the subsequent image displayed on the screen;
   (viii) upon the target skin lesion not being present within the subsequent image, instruct the user of the system to move the handheld inspection device away from the target skin lesion; and
   (ix) repeat steps (iv)-(viii) with the subsequent image being the current image, until a close-up inspection criterion is met.

2. The system of claim 1, wherein the close-up inspection criterion is one or more of the following: (a) a distance of the handheld inspection device from the skin surface is equal to or smaller than a predefined distance, or (b) an image of the target skin lesion occupies a predefined size or percentage of the screen.

3. The system of claim 1, wherein the handheld inspection device comprises a laser capable of projecting a laser beam, and wherein the processing circuitry is further configured to cause the laser to project the laser beam within the target skin lesion for performing one or more of the following: (a) identifying the target skin lesion; (b) measuring a distance between the handheld inspection device and the skin surface; or (c) measuring an angle between an optical axis of the camera and the skin surface.

4. The system of claim 1, wherein the handheld inspection device comprises a laser capable of projecting a laser beam parallel to an optical axis of the camera and in a known distance from the optical axis, the laser beam producing a visible laser dot on the skin surface, and wherein the processing circuitry is further configured to:
   cause the laser to project the laser beam, thereby producing the laser dot on the skin surface; and
   determine dimensions of the target skin lesion utilizing the size of the laser dot utilizing the known distance and a determined distance between a center of the current image and the laser dot.

5. The system of claim 1, wherein the handheld inspection device comprises a mechanical stopper causing the camera to be at a known distance from the skin surface upon the mechanical stopper making contact with the skin surface, and wherein the processing resource is further configured to determine dimensions of the target skin lesion utilizing the known distance.

6. The system of claim 1, wherein the handheld inspection device comprises an illuminator capable of illuminating at least part of the region, and wherein the processing circuitry is further configured to cause the illuminator to illuminate the at least part of the region.

7. The system of claim 1, wherein the processing circuitry is further configured to perform digital dermatoscopy of the target skin lesion.

8. The system of claim 1, wherein the processing circuitry is further configured to extract features of the target skin lesion.

9. The system of claim 1, wherein the processing circuitry, the camera and the screen are comprised within a housing of the handheld inspection device.

10. The system of claim 1, further comprising a computer that is separate from the handheld inspection device, and wherein the screen and the processing circuitry form part of the computer.

11. A method for inspection of at least one skin lesion within a region on a skin surface, the region containing multiple skin lesions, the method comprising:
   (i) acquiring, by at least one processing circuitry, using a camera comprised within a handheld inspection device, a current image, the current image including the region;
   (ii) displaying, by the processing circuitry, the image on a screen;
   (iii) marking, by the processing circuitry, a target skin lesion of the skin lesions on the image displayed on the screen, to visually distinguish the target skin lesion from other skin lesions within the region, the target skin lesion being selected for close-up inspection;
   (iv) acquiring, by the processing circuitry, using the camera, while the handheld inspection device is moved toward the skin surface, a subsequent image, subsequent to the current image, the subsequent image acquired by the camera from a first distance from the target skin lesion, smaller than a second distance from the target skin lesion from which the current image was acquired;
   (v) displaying, by the processing circuitry, the subsequent image on the screen;
   (vi) checking, by the processing circuitry, presence of the target skin lesion within the subsequent image;
   (vii) upon the target skin lesion being present within the subsequent image, marking, by the processing circuitry, the target skin lesion on the subsequent image displayed on the screen;
   (viii) upon the target skin lesion not being present within the subsequent image, instructing, by the processing circuitry, the user of the system to move the handheld inspection device away from the target skin lesion; and (ix) repeating, by the processing circuitry, steps (iv)-(viii) with the subsequent image being the current image, until a close-up inspection criterion is met.

12. The method of claim 11, wherein the close-up inspection criterion is one or more of the following: (a) a distance of the handheld inspection device from the skin surface is equal to or smaller than a predefined distance, or (b) an image of the target skin lesion occupies a predefined size or percentage of the screen.

13. The method of claim 11, further comprising causing, by the processing circuitry, a laser comprised within the handheld inspection device to project a laser beam within the target skin lesion for performing one or more of the following: (a) identifying the target skin lesion; (b) measuring a distance between the handheld inspection device and the skin surface; or (c) measuring an angle between an optical axis of the camera and the skin surface.

14. The method of claim 11, further comprising:
causing, by the processing circuitry, a laser capable of projecting a laser beam parallel to an optical axis of the camera and in a known distance from the optical axis, the laser beam producing a visible laser dot on the skin surface, to project the laser beam, thereby producing the laser dot on the skin surface; and
determining, by the processing circuitry, dimensions of the target skin lesion utilizing the size of the laser dot utilizing the known distance and a determined distance between a center of the current image and the laser dot.

15. The method of claim 11, further comprising determining, by the processing circuitry, dimensions of the target skin lesion, utilizing a known distance between a mechanical stopper connected to the handheld inspection device and causing the camera to be at the known distance from the skin surface upon the mechanical stopper making contact with the skin surface.

16. The method of claim 11, further comprising illuminating, by the processing circuitry, the at least part of the region using an illuminator comprised within the handheld inspection device and capable of illuminating at least part of the region.

17. The method of claim 11, further comprising performing digital dermatoscopy of the target skin lesion.

18. The system of claim 11, further comprising extracting features of the target skin lesion.

* * * * *